United States Patent [19]

Martel et al.

[11] 4,412,069

[45] Oct. 25, 1983

[54] PROCESS FOR PREPARING CYCLOPROPANE CARBOXYLIC ACID DERIVATIVES

[75] Inventors: Jacques Martel, Bondy; Jean Tessier, Vincennes; Jean-Pierre Demoute, Montreuil-sous-Bois, all of France

[73] Assignee: Roussel Uclaf, Paris, France

[21] Appl. No.: 58,273

[22] Filed: Jul. 17, 1979

[30] Foreign Application Priority Data

Jul. 24, 1978 [FR] France ............................... 78 21813

[51] Int. Cl.$^3$ ............................................ C09B 23/00

[52] U.S. Cl. ................................... 542/429; 424/274; 542/426; 562/506

[58] Field of Search ................ 542/426, 429; 424/274; 562/506

[56] References Cited

U.S. PATENT DOCUMENTS

| | | | |
|---|---|---|---|
| 3,714,153 | 1/1973 | Martel et al. | 542/426 |
| 3,723,469 | 3/1973 | Martel | 562/506 |
| 3,842,177 | 10/1974 | Martel et al. | 424/274 |
| 4,014,918 | 3/1977 | Martel | 562/506 |
| 4,166,063 | 8/1979 | Martel et al. | 260/343.37 |

*Primary Examiner*—Arthur P. Demers
*Attorney, Agent, or Firm*—Hammond & Littell, Weissenberger and Muserlian

[57] ABSTRACT

A novel process for the preparation of a compound of the formula

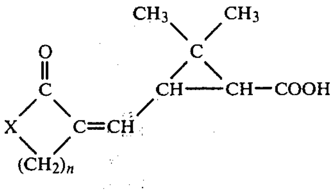

I wherein X is selected from the group consisting of oxygen and sulfur and n is 1,2 or 3 comprising reacting in an organic solvent in the presence of a strong base the lactone of cis 2,2-dimethyl-3S-(dihydroxymethyl)-cyclopropane-1R-carboxylic acid with a compound of the formula

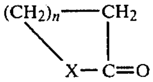

III to obtain a compound of the formula

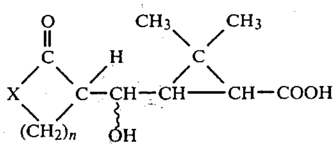

IV reacting the latter with an acid agent in an apolar organic solvent to obtain a compound of the formula

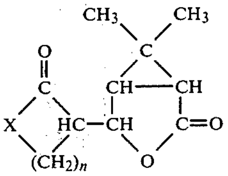

and reacting the latter with a basic agent in an apolar organic solvent to obtain a compound of formula I useful for the preparation of insecticidal esters and the novel compounds of formula I wherein n is 1 or 3.

8 Claims, No Drawings

PROCESS FOR PREPARING CYCLOPROPANE CARBOXYLIC ACID DERIVATIVES

STATE OF THE ART

French Pat. No. 2,045,177 describes the preparation of (1R,3S) 3-[(dihydro-2-oxo-3(2H)-furanylidene)-methyl]-2,2-dimethyl-cyclopropane-1-carboxylic acid by the Wittig reaction with 2,2-dimethyl-3S-formyl-cyclopropane-1 R-carboxylic acid and 2-oxo-3-oxa-cyclopentylidene triphenyl phosphorane.

French Pat. No. 2,097,244 describes the preparation of (1R,3S) 3-[(dihydro-2-oxo-3(2H)-thienylidene)-methyl]-2,2-dimethyl-cyclopropane-1-carboxylic acid by the Wittig reaction with 2,2-dimethyl-3S-formyl-cyclopropane-1R-carboxylic acid and 2-oxo-3-thia-cyclopentylidene triphenyl phosphorane.

OBJECTS OF THE INVENTION

It is an object of the invention to provide a simple and industrial possible process for the preparation of the compounds of formula I from readily available starting materials.

It is also an object of the invention to provide the novel compounds of formula I wherein n is 1 or 3.

These and other objects and advantages of the invention will become obvious from the following detailed description.

THE INVENTION

The novel process of the invention for the preparation of a compound of the formula

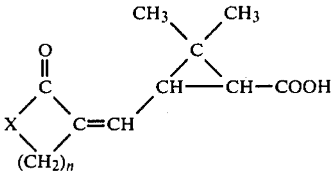

I wherein X is selected from the group consisting of oxygen and sulfur and n is 1,2 or 3 comprises reacting in an organic solvent in the presence of a strong base the lactone of cis 2,2-dimethyl-3S-(dihydroxymethyl)-cyclopropane-1R-carboxylic acid with a compound of the formula

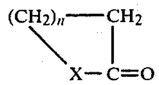

III to obtain a compound of the formula

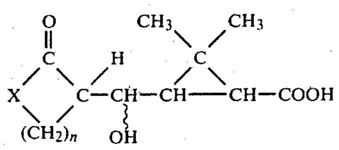

IV reacting the latter with an acid agent in an apolar organic solvent to obtain a compound of the formula

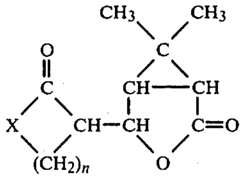

V and reacting the latter with a basic agent in an apolar organic solvent to obtain a compound of formula I.

Especially preferred is the process wherein X is sulfur. The strong basic agent is preferably selected from the group consisting of alkali metal alcoholates, alkali metal amides, alkali metal hydrides and alkali metals, and the organic solvent used for the condensation with the compound of formula III is preferably tetrahydrofuran.

The acid agent is preferably selected from the group consisting of p-toluene sulfonic acid, benzene sulfonic acid, hydrochloric acid and sulfuric acid and the organic apolar solvent used is preferably an aromatic hydrocarbon such as benzene or toluene.

The basic agent is preferably a tertiary base such as triethylamine or pyridine and the organic apolar solvent is preferably an aromatic hydrocarbon such as benzene or toluene.

A preferred mode of the process to prepare the compounds of formula I wherein X is sulfur and n is 2 comprises reacting the lactone of cis 2,2-dimethyl-3S-(dihydroxymethyl)-cyclopropane-1R-carboxylic acid with dihydro-3(2H)-thiophenone in tetrahydrofuran in the presence of potassium tert.-butylate to obtain (1R,3S) 3-[(dihydro-2-oxo-3(2H)-thienyl)-hydroxymethyl]-2,2-dimethyl-cyclopropane-1-carboxylic acid, reacting the latter in benzene with p-toluene sulfonic acid to obtain (1R,4R,5S)-4-(dihydro-2-oxo-3(2H)-thienyl)-6,6-dimethyl-3-oxabicyclo-(3,1,0)-hexan-2-one and reacting the latter with triethylamine in benzene to obtain (1R,3S)-3-[(dihydro-2-oxo-3(2H)-thienylidene)-methyl]-2,2-dimethyl-cyclopropane-1-carboxylic acid.

In an analogous manner, the use of 2-thietanone or tetrahydro-(2H)-thiopyran-2-one in place of dihydro-2(3H)-thiophene results in (1R,3S) 3-[(2-oxo-3-thietanylidene)-methyl]-2,2-dimethyl-cyclopropane-1-carboxylic acid or (1R,3S) 3-[(2-oxo-tetrahydro-3(2H)-thiopyranylidene)-methyl]-2,2-dimethyl-cyclopropane-1-carboxylic acid, respectively.

In an analogous manner, the use of 2-oxetanone or dihydro-2(3H)-furanone or tetrahydro-(2H)-pyran-2-one in place of dihydro-2(3H)-thiophenone results in (1R,3S) 3-[(2-oxo-3-oxetanylidene)-methyl]-2,2-dimethyl-cyclopropane-1-carboxylic acid, (1R,3S) 3-[(dihydro-2-oxo-3(2H)-furanylidene)-methyl]-2,2-dimethyl-cyclopropane-1-carboxylic acid and (1R,3S) 3-[(2-oxo-tetrahydro-3(2H)-pyranylidene)-methyl]-2,2-dimethyl-cyclopropane-1-carboxylic acid, respectively.

The new products of the invention of formula I are (1R,3S) 3-[(2-oxo-3-thietanylidene)-methyl]-2,2-dimethyl-cyclopropane-1-carboxylic acid, (1R,3S) 3-[(2-oxo-tetrahydro-3(2H)-thiopyranylidene)-methyl]-2,2-dimethyl-cyclopropane-1-carboxylic acid, (1R,3S) 3-[(2-oxo-3-oxetanylidene)-methyl]-2,2-dimethyl-cyclopropane-1-carboxylic acid and (1R,3S) 3-[(2-oxo-tetrahydro-3(2H)-pyranylidene)-methyl]-2,2-dimethyl-cyclopropane-1-carboxylic acid.

The process of the invention has the advantage of using readily available starting materials which is not the case of the phosphoranes of the prior art and the intermediates do not have to be isolated. The operations are particularly simple and easily commercialized.

Moreover, the overall yield of process is clearly greater than that of the prior art processes. The condensation of the compound of formula III with the lactone of cis 2,2-dimethyl-3S-(dihydroxymethyl)-cyclopropane-1R-carboxylic acid which has the formula

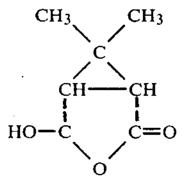

II results in very high yields under extremely simple conditions which, a priori, could not be expected. Generally, lactones or thiolactones of the type of formula III do not easily react with an aldehyde group such as exists in the lactone form of formula II. It is known that for this type of reaction with a compound of formula III with a compound containing an aldehyde group to proceed easily with high yields, it is necessary that the aldehyde group be fixed on an aromatic ring.

In the following examples there are described several preferred embodiments to illustrate the invention. However, it is to be understood that the invention is not intended to be limited to the specific embodiments.

EXAMPLE 1

(1R,3S) 3-[(dihydro-2-oxo-3(2H)-thienylidene)-methyl]-2,2-dimethyl-cyclopropane-1-carboxylic acid

STEP A: (1R,3S) 3-[(dihydro-2-oxo-3(2H)-thienyl)-hydroxymethyl]-2,2-dimethyl-cyclopropane-1-carboxylic acid A mixture of 2.84 g of the lactone of cis 2,-dimethyl-3S-dihydroxymethyl-cyclopropane-1R-carboxylic acid, 2.2 g of dihydro-3(2H)-thiophenone and 50 ml of tetrahydrofuran under an inert atmosphere was cooled to −60° C. and a solution of 4.5 g of potassium tert.-butylate in 35 ml of anhydrous tetrahydrofuran was added thereto over 30 minutes. The mixture was stirred at −60° C. for one hour and then 50 ml of aqueous N hydrochloric acid were slowly added thereto while keeping the temperature below −20° C. The mixture was diluted with water and was extracted with methylene chloride. The organic phase was washed with water, dried over sodium sulfate, filtered and evaporated to dryness to obtain 6.2 g of raw (1R,3S) 3[(dihydro-2-oxo-3(2H)-thienyl)-hydroxymethyl]-2,2-dimethyl-cyclopropane-1-carboxylic acid which was used as is for the next step.

STEP B: (1R,4R,5S) 4-[dihydro-2-oxo-3-(2H)-thienyl]-6,6-dimethyl-3-oxabicyclo-(3,1,0)-hexan-2-one 50 mg of p-toluene sulfonic acid were added to a solution of 6.2 g of the product of Step A in 70 ml of benzene and the mixture was refluxed for 90 minutes while removing the water of reaction by passing the condensed solvent through silica gel to obtain a solution of (1R,4R,5S) 4-[dihydro-2-oxo-3-(2H)-thienyl]-6,6-dimethyl-3-oxabicyclo-(3,1,0)-hexan-2-one which was used as is for the next step.

STEP C: (1R,3S) 3-[(dihydro-2-oxo-3(2H)-thienylidene)-methyl]-2,2-dimethyl-cyclopropane-1-carboxylic acid A mixture of the solution of Step B and 6 ml of triethylamine was refluxed for 3 hours and was then cooled and poured into 2 N aqueous hydrochloric acid. The decanted organic phase was washed with water, dried and evaporated to dryness. The residue was taken up in 20 ml of hot methylene chloride and after the addition of 30 ml of n-heptane thereto, the mixture was cooled to 5° C. and vacuum filtered. The recovered product was washed with heptane and dried to obtain 3.025 g of (1R,3S) 3-[(dihydro-2-oxo-3(2H)-thienylidene)-methyl]-2,2-dimethyl-cyclopropane-1-carboxylic acid melting at 162° C.

RMN Spectrum (deuterochloroform): peaks at 1.29–1.38 ppm (hydrogens of 2-methyls of cyclopropyl); at 1.83–2.08 ppm (1- and 3-hydrogens of cyclopropyl); at 2.83–3.5 ppm (hydrogens of cyclopentyl); and at 6.77–6.92 ppm (1′-hydrogen of ethyl side chain).

Various modifications of the process and products of the invention may be made without departing from the spirit or scope thereof and it should be understood that the invention is intended to be limited only as defined in the appended claims.

We claim:

1. A process for the preparation of a compound of the formula

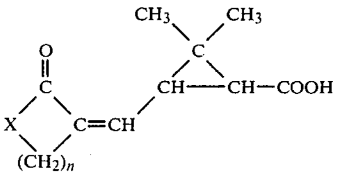

I wherein X is selected from the group consisting of oxygen and sulfur and n is 1,2 or 3 comprising reacting in an organic solvent in the presence of a strong base the lactone of cis 2,2-dimethyl-3S-(dihydroxymethyl)-cyclopropane-1R-carboxylic acid with a compound of the formula

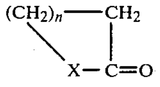

to obtain a compound of the formula

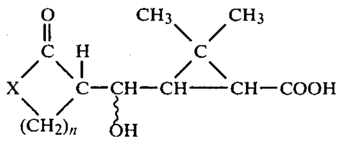

reacting the latter with an acid agent in an apolar organic solvent to obtain a compound of the formula

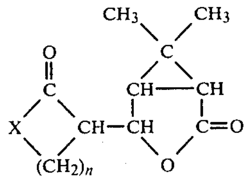

and reacting the latter with a basic agent in an apolar organic solvent to obtain a compound of formula I 2. The process of claim 1 wherein X is sulfur.

3. The process of claim 1 wherein the strong basic agent is selected from the group consisting of alkali metal alcoholates, alkali metal amides, alkali metal hydrides and alkali metals.

4. The process of claim 3 wherein the organic solvent is tetrahydrofuran.

5. The process of claim 1 wherein the acid agent is selected from the group consisting of p-toluene sulfonic acid, benzene sulfonic acid, hydrochloric acid and sulfuric acid and the organic apolar solvent is an aromatic hydrocarbon.

6. The process of claim 1 wherein the basic agent is a tertiary base and the organic apolar solvent is an aromatic hydrocarbon.

7. The process of claim 6 wherein the tertiary base is pyridine or triethylamine.

8. The process of claim 1 wherein n is 2.

* * * * *